(12) United States Patent
Maguire et al.

(10) Patent No.: US 9,862,922 B2
(45) Date of Patent: Jan. 9, 2018

(54) RAPID GROWTH ACTIVATOR

(71) Applicants: Richard H. Maguire, Sarasota, FL (US); Charles F. Bruno, Cranbury, NJ (US)

(72) Inventors: Richard H. Maguire, Sarasota, FL (US); Charles F. Bruno, Cranbury, NJ (US)

(73) Assignees: PolyOrganic Technologies Corporation, Cranbury, NJ (US); Ultra-Grow Technologies, Inc., Sarasota, FL (US)

( * ) Notice: Subject to any disclaimer, the term of this patent is extended or adjusted under 35 U.S.C. 154(b) by 0 days.

(21) Appl. No.: 15/269,070

(22) Filed: Sep. 19, 2016

(65) Prior Publication Data

US 2017/0081631 A1    Mar. 23, 2017

Related U.S. Application Data

(60) Provisional application No. 62/219,694, filed on Sep. 17, 2015.

(51) Int. Cl.
| | |
|---|---|
| *C12N 1/14* | (2006.01) |
| *A01N 63/00* | (2006.01) |
| *A01N 63/02* | (2006.01) |
| *C12N 1/20* | (2006.01) |
| *C12N 1/18* | (2006.01) |

(52) U.S. Cl.
CPC ............... *C12N 1/20* (2013.01); *A01N 63/00* (2013.01); *A01N 63/02* (2013.01); *C12N 1/14* (2013.01); *C12N 1/18* (2013.01)

(58) Field of Classification Search
None
See application file for complete search history.

(56) References Cited

PUBLICATIONS

De Brito Alvarez, et al. Appl Environ Microbiol 61:194 (1995).*
Zaccardelli et al., "The development and suppressive activity of soil microbial communities under compost amendment", J Soil Sci Plant Nutr 13: 730-742 (2013).*

* cited by examiner

*Primary Examiner* — Robert A Wax
*Assistant Examiner* — Thor Nielsen
(74) *Attorney, Agent, or Firm* — Botkin & Hall

(57) ABSTRACT

A composition of matter is provided having *bacillus subtilis, bacillus pumilus, bacillus coagulans, paenibacillus polymyxa, pseudomonas fluorescens, streptomycetes griseus, saccharomyces cerevisiae, trichoderma reesei,* and *trichoderma harzianum*. The composition further includes dextrose, sucrose, brewer's yeast extract, humic acid, and kelp. Applying the composition in the proximity of the root system allows the composition to colonize the rhizosphere. The composition is generated by individually culturing the components, combining them with diatomaceous earth, and drying to encapsulate the components.

4 Claims, 4 Drawing Sheets

RAPID GROWTH ACTIVATOR

CROSS REFERENCE TO RELATED APPLICATIONS

This application claims the benefit of U.S. Provisional Application No. 62/219,694 filed Sep. 17, 2015, the disclosures of which are hereby incorporated by reference.

BACKGROUND OF THE INVENTION

Over the last 500 million years plants and beneficial soil microorganisms have developed a symbiotic relationship. When plants photosynthesize they release carbon exudates into the rhizosphere, which microorganisms utilize as a food source. The beneficial microbes surround the root system to sequester this carbon source and in return, the microorganisms nourish the roots, recycle nutrients, improve the surrounding soil structure and solubilize minerals for plant availability.

Unfortunately today many soils are grossly out of balance and are devoid of beneficial microbial populations. This is primarily due to an over reliance on pesticides and inorganic fertilizers as both adversely affect the delicate microbial balance found in healthy soil profiles.

Throughout the year the soil is exposed to pesticides, high salt fertilizer, environmental pollution, drought, compaction, temperature extremes, and other environmental conditions all of which can negatively impact the microorganisms. This applies to both indigenous as well as laboratory grown organisms. In short, the soil food web must be re-energized periodically to maintain optimum plant growth.

At certain times of the year, the soil requires greater biological activity in order to grow healthy plants. This includes the establishment phase, flowering phase, plant stress, and when the environment conditions favor disease (warmth, dampness, and high humidity). Regardless of the phase, it is always advisable to increase biological activity with an extra shot of beneficial organisms.

SUMMARY OF THE INVENTION

Rapid Growth Activator (RGA) is an all-natural product specifically formulated to increase biological activity in the rhizosphere and restore a productive root system to distressed plants. Diseased plants, particularly ones infected with HLB (citrus greening disease) are positively impacted by RGA. Further, it is a comprehensive microbial system comprised of beneficial soil bacteria, actinobacteria, fungi, and microbial synergists to promote rapid microbial establishment in the rhizosphere. It is produced via a sui generis fermentation process so as to maximize the production of bioactive secondary metabolites to further enhance overall product performance.

Rapid Growth Activator (RGA) was specifically formulated to re-establish these beneficial microbial populations and provide the soil with the necessary components to promote vigorous plant growth, particularly citrus plants.

RGA provides enumerable benefits to both the soil and the plant. Specifically, the microbial system will promote root growth, enhance root architecture, minimize the incidence of nutrient leaching, aid in nutrient cycling, enhance nutrient absorption, solubilize & mineralize nutrients (including phosphorous) for plant availability, stimulate plant growth, and provide increased resistance to abiotic stress.

This invention has more microorganism diversity than others previously available, manufactured, or formulated. The procedure used to preserve the metabolites and root stimulating hormones is unique to this invention. This invention not only provides growth stimulator but also antibiotics that suppress or stop the growth of gram negative and positive bacteria that destroy root development. The *streptomyces* in RGA produce Streptomycin, which is an antibiotic that kills Gram negative bacteria such as *Candidatus Liberibacter*, which is thought to be the main cause of citrus roots dying.

BRIEF DESCRIPTION OF THE DRAWINGS

A preferred embodiment of this invention has been chosen wherein.

DESCRIPTION OF THE PREFERRED EMBODIMENT

Figure 2:
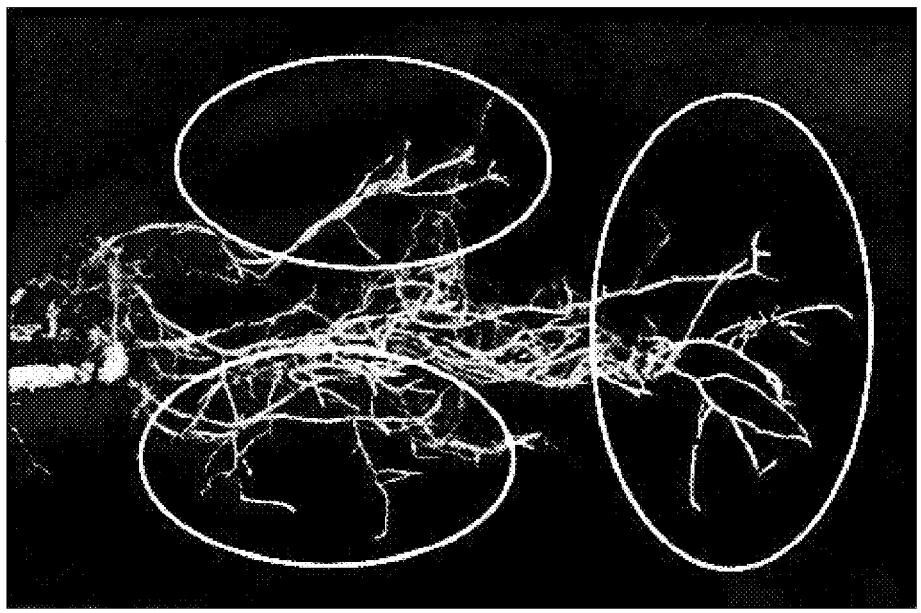
FIG. 2 shows the results of the root system of a Valencia sweet orange tree as treated by RGA in eight treatments.
Figure 1:
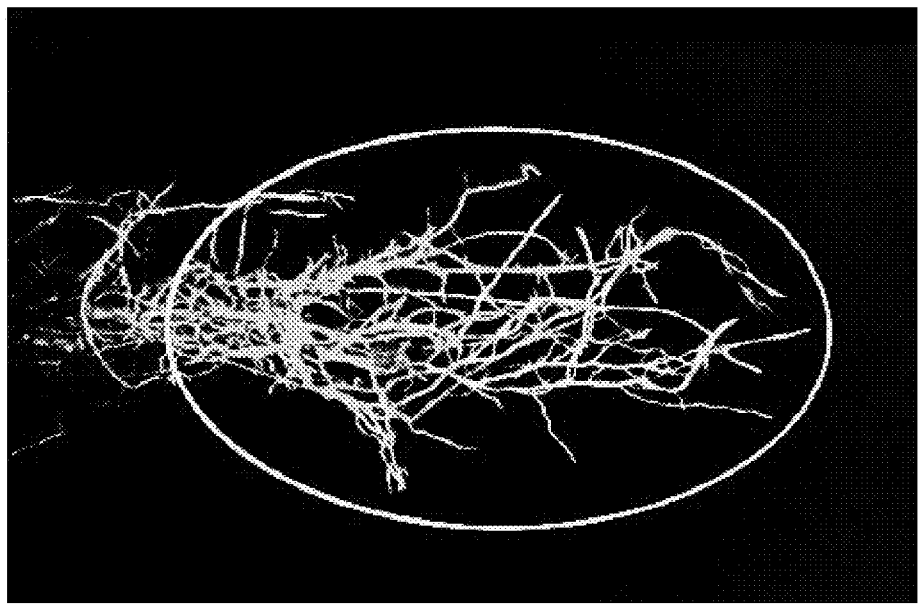
FIG. 1 shows the results of the root system of a Valencia sweet orange tree as treated by RGA in two treatments.
Figure 4:
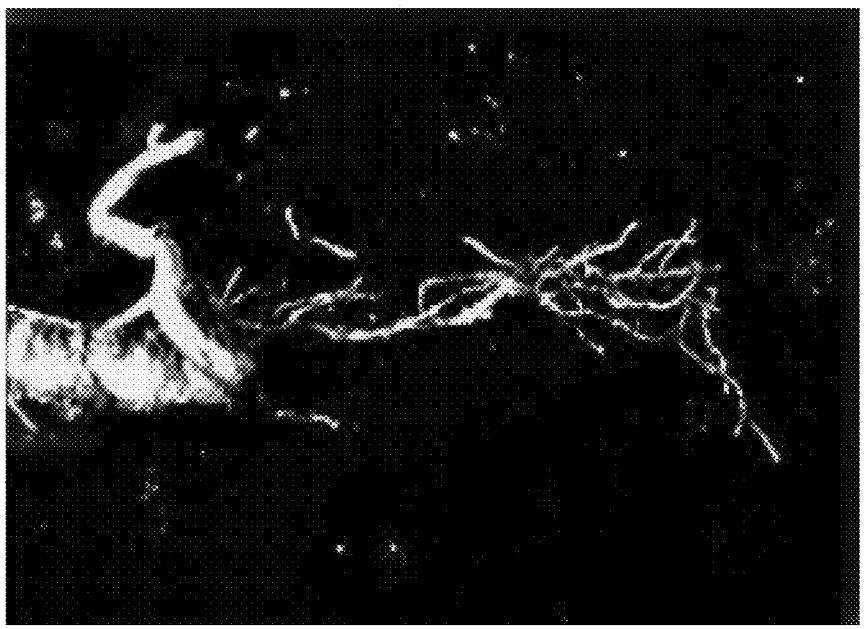
FIG. 4 shows the results after ten months of a HLB infected root system of a citrus tree root system as untreated and receiving only water and liquid fertilizer.
Figure 3:
FIG. 3 shows the results after ten months of a HLB infected root system of a citrus tree root system as untreated and receiving only water and liquid fertilizer.
Figure 6:
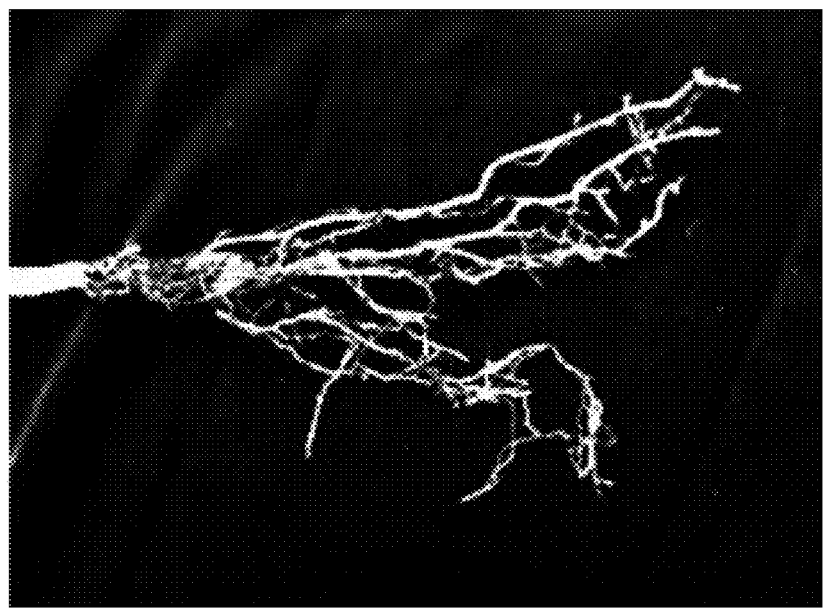
FIG. 6 shows the results after ten months of a HLB infected root system of a citrus tree root system as untreated and receiving only water and liquid fertilizer.
Figure 5:
FIG. 5 shows the results after ten months of a HLB infected root system of a citrus tree root system as untreated and receiving only water and liquid fertilizer.
Figure 8:
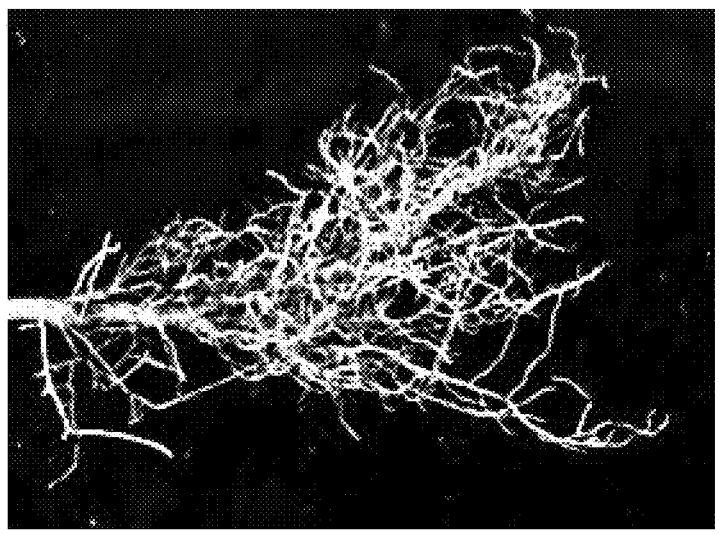
FIG. 8 shows the results after ten months of a HLB infected root system of a citrus tree root system treated by RGA at 2 week intervals.
Figure 7:
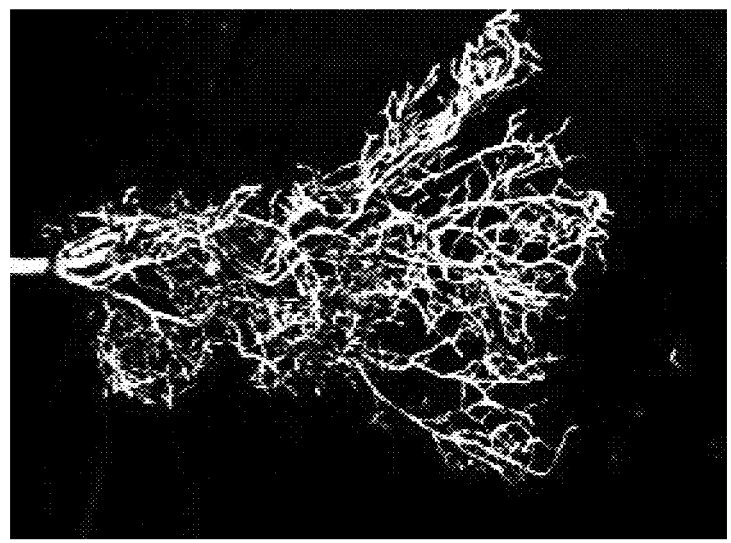
FIG. 7 shows the results after ten months of a HLB infected root system of a citrus tree root system treated by RGA at 2 week intervals.

Overall, RGA is a combination of ingredients, including non-plant food, inert materials, bacteria, and fungus. RGA is primarily directed towards use with citrus trees but can be applied to other plants. The concentration of each of these materials is listed hereinafter. For clarity, a Colony Forming Unit (CFU) is a number of viable bacteria or fungi in a given measured amount. In this specification, grams and pounds are used but other measuring methods and amounts are contemplated.

The general rate of application is 2.3 kg (5 lbs) per acre pre-diluted in a sufficient volume of water to achieve desired coverage. Desired coverage equates is 14-16 grams per tree assuming 140-160 trees per acre. Irrigate immediately to bring product into soil profile. Optimum results achieved when applied morning or evening. To prevent run-off and allow the RGA to enter the rhizosphere, avoid applying product just prior to excessive rainfall.

RGA includes the following non plant food ingredients roughly in concentrations of: *bacillus subtilis* at approximately 80,000,000 CFU per gram, *bacillus pumilus* at approximately 80,000,000 CFU per gram, *bacillus coagulans* at approximately 80,000,000 CFU per gram, *paenibacillus polymyxa* at approximately 80,000,000 CFU per gram, *pseudomonas fluorescens* at approximately 80,000,000 CFU per gram, *streptomycetes griseus* at approximately 80,000,000 CFU per gram, *saccharomyces cerevisiae* at approximately 80,000,000 CFU per gram, *trichoderma reesei* at approximately 40,000,000 CFU per gram, and *trichoderma harzianum* at approximately 40,000,000 CFU per gram.

RGA includes the following inert ingredients roughly in concentrations of: 50.00% dextrose, 21.25% sucrose, 2.00% brewer's yeast extract, 1.00% humic acid (also known as leonardite), 1.00% kelp (also known as *ascophyllum nodosum*). The sucrose, dextrose, and glucose serve as nutrients for the microorganisms and other active ingredients. The brewer's yeast contains vitamins, trace minerals, and other nutrients. Humic acid improves nutrient uptake, increases root vitality, increases chlorophyll synthesis, increases fertilizer retention, stimulates beneficial microbial activity by providing a carbon source, and adds essential organic material necessary for water retention, thus improving root growth and enhancing the sandy soil's ability to retain and not leach out vital plant nutrients. *Ascophyllum nodosum* is used as an organic and mainstream fertilizer for plants due to its combination of both micronutrients such as N, P, K, Ca, Mg, and S and micronutrients such as Mn, Cu, Fe, Zn. It is also a host to cytokinins, auxin-like gibberellins, betaines, mannitol, organic acids, polysaccharides, amino acids, and proteins which are very beneficial and widely used in agriculture.

GENUS: *BACILLUS* (BACTERIA): These are motile organisms which colonize the rhizosphere to feed on root exudates. These produce a variety of secondary metabolites such as antibiotics & enzymes which have an inhibitory effect on pathogenic fungi and other antimicrobial properties. They produce protein and peptide based compounds (bacteriocins) which have an inhibitory effect on pathogenic bacteria.

*Bacillus subtilis*: This bacterium is commonly found in soil and the gastrointestinal tract of ruminants and humans. The *bacillus subtilis* produces plant growth regulatory compounds (PGR) that stimulate root & shoot growth. It produces numerous enzymes & organic acids which promote nutrient cycling, nutrient solubilization & nutrient mineralization (improves nutrient availability—especially P). It also produces polysaccharides which create micro-aggregates in soil profile (enhances soil structure). This bacteria is capable of stimulating Induced Systemic Resistance (ISR) in plants whereby ISR stimulate the plants natural defenses against stress and pathogenic intrusions.

*Bacillus pumilus*: Growth of this bacterium on plant roots prevents *Rhizoctonia* and *Fusarium* spores from germinating. Plant growth regulatory compounds (PGR) are produced which stimulate root & shoot growth. These produce numerous enzymes & organic acids which promote nutrient cycling, nutrient solubilization & nutrient mineralization (improves nutrient availability especially P). To enhance soil structure, polysaccharides are produced which create micro-aggregates in soil profile. These are capable of stimulating Induced Systemic Resistance (ISR) in plants whereby ISR stimulates the plants natural defenses against stress and pathogenic intrusions.

*Bacillus coagulans*: This bacterium is known to produce lactic acid. This bacteria produces plant growth regulatory compounds (PGR) which stimulate root & shoot growth and produces numerous enzymes & organic acids which promotes nutrient cycling, nutrient solubilization & nutrient mineralization (improves nutrient availability especially P). Further, it produces polysaccharides which create micro-aggregates in soil profile (enhances soil structure). This bacteria is capable of stimulating Induced Systemic Resistance (ISR) in plants whereby ISR stimulates the plants natural defenses against stress and pathogenic intrusions.

*Paenibacillus polymyxa*: This bacterium is known to fix nitrogen and help protect plants from pathogens. It also is known to disrupt biofilms of *bacillus subtilis*. Produces plant growth regulatory compounds (PGR) which stimulate root & shoot growth. Produces numerous enzymes & organic acids which promotes nutrient cycling, nutrient solubilization & nutrient mineralization (improves nutrient availability). Produces polysaccharides which create micro-aggregates in soil profile (enhances soil structure). Capable of stimulating Induced Systemic Resistance (ISR) in plants whereby ISR stimulates the plants natural defenses against stress and pathogenic intrusions. Free living nitrogen fixers which convert atmospheric di-nitrogen (N2) into plant available ammonia (NH3).

GENUS: *PSEUDOMONAS* (BACTERIA): These are motile organisms which colonize the rhizosphere to feed on root exudates.

*Pseudomonas fluorescens*: This is known to protect the roots against certain parasitic fungi. Versatile metabolism which allows organisms to reproduce proficiently in rhizosphere. These produce a variety of secondary metabolites (antibiotics & enzymes) which have an inhibitory effect on both pathogenic fungi & bacteria. Produces plant growth regulatory compounds (PGR) which stimulate root & shoot growth. Particularly adept at solubilizing phosphorous in the soil profile. The increased P availability promotes root growth and enhances root architecture. Capable of stimulating Induced Systemic Resistance (ISR) in plants whereby ISR stimulates the plants natural defenses against stress and pathogenic intrusions.

GENUS: *STREPTOMYCETES* (ACTINOBACTERIA)

*Streptomyces griseus:* Filamentous bacteria. This is commonly present in soil. Prolific at producing antifungal-antibacterial secondary metabolites which are antagonistic to pathogenic fungi and bacteria. Prolific enzyme producer (promotes nutrient cycling). Produces plant growth promoting compounds (PGR) that stimulate root and shoot growth. Enhances soil structure through the creation of macro-aggregates. PGR weave their thread like hyphae around micro-aggregates created by bacteria.

GENUS: *TRICHODERMA* (FUNGI)

*Trichoderma harzianum*: Filamentous fungi. This is commonly used as a fungicide to suppress disease and manufacture enzymes. Extremely efficient at producing cellulase—the enzyme that degrades cellulose (contributes to nutrient cycling). Produces cell wall lytic enzymes which provide the organism with potent antifungal properties. Produces antibacterial acids which have an inhibitory effect on pathogenic bacteria. Solubilizes phosphorous in the soil. The increased P availability promotes root growth and enhances root architecture.

*Trichoderma reesei*: Filamentous fungi. Extremely efficient at producing cellulase (contributes to nutrient cycling). Produces cell wall lytic enzymes such as chitinases & B-glucanases, which provide the organism with potent antifungal properties. Produces antibacterial acids which have an inhibitory effect on pathogenic bacteria. Solubilizes phosphorous in the soil. The increased P availability promotes root growth and enhances root architecture.

*Saccharomyces cerevisiae*: Efficient at breaking down carbohydrates—contributes to carbon cycling in soil profile. This is a species of yeast that can grow on glucose. Stimulates plant growth through the production of Plant Growth Regulators (PGR). Produces antibacterial & antifungal secondary metabolites which are antagonistic to pathogenic bacteria & fungi.

MICROBIAL SYNERGISTS: Contains a blend of targeted microbial synergists that are enzymes and metabolites of microorganisms contained within RGA. Synergists promote rapid establishment of beneficial soil organisms in the rhizosphere. These provide microbial systems with essential nutrients during their critical lag & log phases of development. Allows for efficient transformation from laboratory to soil micro-climates.

SECONDARY METABOLITES: Secondary metabolites are organic compounds produced by bacteria, actinobacteria, & fungi which are not directly related to the growth, development, reproduction or homeostasis of the organism. Secondary metabolites include but are not limited to essential compounds such as enzymes, antibiotics, organic acids & plant growth regulators. Nearly every positive attribute associated with a beneficial soil organism can be attributed to the secondary metabolites the organism produces in Rapid Growth Activator (RGA). RGA is manufactured in such a way as to maximize secondary metabolite production by the organisms in the formula.

RGA is formulated with *bacillus, pseudomonas, trichoderma, streptomyces* and *saccharomyces cerevisiae* that have been cultured using aseptic conditions that are disclosed hereinafter. *bacillus subtilis, bacillus pumilus, bacillus coagulans,* and *paenibacillus polymyxa* are the bacilli formulated in the RGA product. These Bacilli all produce protein and peptide based compounds that have an inhibitory effect on pathogenic bacteria, antibiotics, enzymes and organic acids that improve nutrient availability for plants. These bacilli also produce plant growth regulatory compounds (PGR) that stimulate root and shoot growth and colonize the rhizosphere to feed on root exudates. Some of these secondary metabolites are constitutive whereas others are produced by induction. Antibiotics such as bacitracin produced by *B. licheniformis*, and polymyxin produced by *B. polymxa* are active against gram positive bacteria, whereas polymyxin and colistin produced by *B. polmyxa* are active against gram negative bacteria. There are several other antibiotics produced by these bacilli in addition to enzymes and metabolites that support health and growth of citrus trees.

In addition to bacilli, RGA is formulated with *pseudomonas fluorescens* that produce a variety of secondary metabolites such as antibiotics and enzymes that have an inhibitory effect on pathogenic bacteria and fungi. *Pseudomonas fluorescens* also stimulate an induced systemic resistance in plants by stimulating the plants natural defense against stress and pathogenic intrusions.

The *streptomyces griseus* produce streptomycin, another antibiotic active against gram negative bacteria. This antibiotic is also active against positive bacteria.

Two species of *trichoderma reesi* and *harzianum* are present in RGA. These fungi produce cell wall lytic enzymes such as chitinase and alpa B-glucanase which hydrolyze the bacterial cell wall of some gram negative bacteria. *Trichoderma* also produces acids that have an inhibitory effect on pathogenic bacteria. The acid products *trichoderma* produces also increases phosphorous availability which promotes root growth.

*Saccharomyces cerevisiae* present in RGA stimulate plant growth through the production of plant Growth Regulators (PGR). This yeast also produces antibacterial secondary metabolites which are antagonistic to pathogenic bacteria and break down carbohydrates that contribute to carbon cycling in soil profile.

All of the microorganisms, microbial synergists and secondary metabolites prepared in the process described below by culturing have been preserved using a procedure that does not inactivate the antibiotics, enzymes, and growth promoters produced by the cultures indicted. In addition, certain products are added to the culture to induce the production of some enzymes produced by specific microorganisms.

The below steps describe the typical manufacturing process for RGA. It is contemplated that the process may be altered. The size of the individual culturing containers is only representative, and can be scaled depending on the quantity desired end product. Many of the products of culturing are finally encapsulated in diatomaceous earth for preservation and storage. Diatomaceous earth is a beneficial medium as it is porous. The pores in the diatomaceous earth provide room for the cultured product and metabolites to be stored.

The preparation for *bacillus subtilis, bacillus pumilus, bacillus coagulans,* and *paenibacillus polymyxa* uses the following steps. A frozen vial (2 ml) of each *bacillus* present in RGA is cultured in a separate 250 ml Erlenmeyer flasks containing 100 ml of sterile tryptic soy broth (soybean—casein digest) at a concentration of 30 grams per liter and a pH of 7.2±0.2. Each inoculated separate flask was placed in a rotary shaker set at a temperature of 30 degrees C. The speed of the rotary shaker is set at 250 RPM. After 96 hours of incubation or until 96% sporulation was achieved, the entire 100 ml of each of the cultured bacilli was added to separate 2800 ml Fernback flasks containing 1000 ml of sterile media containing 30 grams per liter of tryptic soy broth. Each Fernbach flask was then placed in a rotary set at 250 RPM set at a temperature of 30 degree C. After 96 hours of incubation or 96% sporulation, all flasks were aseptically transferred to a single 250 liter vessel containing 185 liters of sterile media. The media contained 15 grams of soybean flour, 5 grams of dextrose, 15 grams of yeast extract, 1 gram of dipotassium phosphate and 0.5 grams of calcium carbonate. The pH of the media was maintained at 7.2 using 5N sodium hydroxide and the agitation speed was set at 300 RPM. The temperature of the culture was controlled at 30 degrees centigrade and the aeration was maintained at an oxygen concentration of 45 percent. After 6 days or when 95 percent sporulation is obtained, the fermentation stops. As is known in the art, sporulation is the phase of growth where the bacillus enters a dormant phase. The broth containing the bacillus was transferred to another vessel and diatomaceous earth was added to the broth to encapsulate bacilli and metabolites produced. The encapsulated bacilli were dried at 30 degrees centigrade to form a first main component of RGA.

A similar procedure was used to culture *pseudomonas fluorescens* using a different media in the 250 Erlenmeyer flask and Fernbach flasks than used for the *bacillus*. The sterile media in the 250 ml Erlenmeyer flasks and 2800 ml Fernbach flasks contained identical media composition 15 gm of soy flour, 5 gm of dextrose, 15 grams of yeast extract, 1 gram of dipotassium, 5 grams of glycerine, and 2 grams of sodium chloride per liter. The pH of the media used in the flasks was 7.2±0.2 and the incubation temperature was 30 degrees centigrade. The composition of the sterile media was the same as that used in the flasks and the pH was maintained at 7.2±0.3. The temperature of the media was maintained at 30 degrees centigrade. The agitation speed was set at 300 RPM. The aeration rate was 40%. After 6 days of growth, the growth stopped and the bacteria and metabolites were encapsulated with diatomaceous earth and dried following the procedure used for the *bacillus*, forming a second main component. The dried pseudomonas and metabolites was stored and used to formulate RGA.

*Streptomyces* were cultured from a frozen vial in the 250 Erlenmeyer flasks with 100 ml of sterile media containing 5 grams of yeast extract, 10 grams of yeast extract, 5 grams of dextrose, 15 grams of soy flour, and 0.5 grams of sodium chloride following the same procedure used for the *bacillus* and *pseudomonas*. The temperature of the *streptomyces* was controlled at 26 degree centigrade until a sporulation of 95-98 percent was achieved. When this level of sporulation was obtained the entire content of each Fernbach flask was transferred to the 250 liter vessel containing 185 liters of sterile media which was identical to that used in the flasks. The pH of the culture was maintained at 7.2±0.02 using 5N (eq/L) sodium hydroxide or 1N hydrochloric acid. When 95-98% sporulation was achieved, diatomaceous earth was added to the broth to encapsulate the *streptomyces* and metabolites produced by *streptomyces* and dried at 30 degrees centigrade to produce a third main component. The dried *streptomyces* and metabolites were then stored to formulate RGA.

The *trichoderma* used in RGA were cultured under conditionals similar to that used for the other microorganisms used to formulate RGA. Frozen vials containing *trichoderma* were cultured in 250 ml Erlenmeyer flasks containing 100 ml of sterile of the following media in grams per liter: 10 grams of dextrose, 7 grams of potato extract, 1 gram of potassium phosphate, 0.5 grams of magnesium sulfate dehydrate, and 5 grams of yeast extract. The incubation temperature was 26 degrees centigrade and the pH of the media was adjusted to 5.6±0.2 using 1N hydrochloric acid or 5N sodium hydroxide. This media composition was also used in the 2800 ml Fernbach flasks. When a 95-98% sporulation rate was obtained, the entire content of inoculated media in the Fernbach flasks was added to a 250 liter vessel containing 185 liter of sterile media identical to that used in the Fernbach flasks except 10 grams per liter of chitosan was added to the media prior to sterilization to stimulate the production of the enzyme chitinase. The temperature of the media was controlled at 26 degrees centigrade. The pH was controlled at 5.6+0.2 using 1N hydrochloric or 5N sodium hydroxide. The aeration was set to provide 40% oxygen. When 95-98% sporulation was obtained, diatomaceous earth was added to the broth. The encapsulated *trichoderma* and metabolites were dried at 30 degrees centigrade to produce a fourth main component. The dried encapsulated *trichoderma* and metabolites were stored and used to formulate RGA.

Five frozen vials of *saccharomyces cerevisiae* were used to inoculate five 250 ml Erlenmeyer flasks containing 100 ml of media. The media in each flask consisted of 3 grams of yeast extract, 3 grams of malt extract, 5 grams of soy flour, and 10 grams of dextrose per liter. Each inoculated flask was placed in a rotary shaker set at 250 rpm at a temperature of 25 degrees centigrade. The pH of the media was 6.2±0.2 and was controlled using 1N hydrochloric acid and 5N sodium hydroxide. When the yeasts in the 250 ml flasks had been cultured for 6 days, the entire 100 ml of inoculated media was transferred to a Fernbach flask containing 1000 ml of media. The media composition in the Fernbach flasks was the same as that used in the 250 ml flask. The rotary shaker was set at 250 rpm. The pH of the media was maintained at 6.2±0.2 and controlled with 1N hydrochloric or 5N sodium hydroxide. The yeasts cultured in the Fernbach flasks were transferred to a 250 liter vessel containing 185 liters of media after 6 days of growth. The media composition in the 250 liter vessel was the same as that used in the Fernbach flasks. The pH of the media was maintained at 6.2. The agitation speed was set a 300 rpm and the temperature was controlled at 26 degrees centigrade. An oxygen concentration of 25% was maintained throughout the fermentation. After 6 days of growth, diatomaceous earth was added to the broth to encapsulate the yeast and metabolites as a fifth main component. The yeast and metabolite slurry was then dried at 30 degrees centigrade and stored to formulate of RGA.

The main components are then all combined with dextrose, sucrose, brewer's yeast extract, humic acid, and kelp.

By encapsulating the microorganisms and broth, all metabolites that have been produced by these cultures are available to provide protection to plants from diseases caused by non-beneficial bacteria. Also, plant growth stimulators produced by these cultures are available to plants.

It is understood that while certain aspects of the disclosed subject matter have been shown and described, the disclosed subject matter is not limited thereto and encompasses various other embodiments and aspects. No specific limitation with respect to the specific embodiments disclosed herein is intended or should be inferred. Modifications may be made to the disclosed subject matter as set forth in the following claims.

What is claimed is:

1. A composition of matter for use with the root systems of plants and trees, said composition comprising:
   about 80,000,000 CFU per gram of *bacillus subtilis*;
   about 80,000,000 CFU per gram of *bacillus pumilus*;
   about 80,000,000 CFU per gram of *bacillus coagulans*;
   about 80,000,000 CFU per gram of *paenibacillus polymyxa*;
   about 80,000,000 CFU per gram of *pseudomonas fluorescens*;
   about 80,000,000 CFU per gram of *streptomycetes griseus*;
   about 80,000,000 CFU per gram of *saccharomyces cerevisiae*;
   about 40,000,000 CFU per gram of *trichoderma reesei*; and
   about 40,000,000 CFU per gram of *trichoderma harzianum*.

2. The composition of matter in claim 1, further comprising dextrose, sucrose, brewer's yeast extract, humic acid, and kelp.

3. A method of increasing biological activity in a rhizosphere, comprising the steps of:
   applying the composition of matter in claim 2 at a rate of 2.3 kg per acre diluted in a volume of water.

4. The method of claim 3, wherein applying 14-16 grams of the composition of matter in claim 2 per plant.

* * * * *